United States Patent [19]

Eager

[11] Patent Number: 5,898,068

[45] Date of Patent: Apr. 27, 1999

[54] MONOCLONAL ANTIBODIES WHICH BIND MEVALONATE KINASE

[75] Inventor: Kendra B. Eager, Cranbury, N.J.

[73] Assignee: Bristol-Myers Squibb Company, New York, N.Y.

[21] Appl. No.: 07/540,251

[22] Filed: May 29, 1990

[51] Int. Cl.$^6$ ............................ C07K 16/40; G01N 33/53
[52] U.S. Cl. ................................ 530/388.26; 530/391.3; 435/7.1; 435/338
[58] Field of Search ...................................... 530/387, 389; 435/240.27, 7.1, 7.4, 388.26, 391.3, 338

[56] References Cited

FOREIGN PATENT DOCUMENTS 0292719  11/1988  European Pat. Off. .
61-126100  6/1986  Japan .

OTHER PUBLICATIONS

Shama Bhat et al., "Purification and Properties of Mevalonate Pyrophosphate Decarboxylase of Rat Liver", *Indian Journal of Biochemistry and Biophysics,* vol. 17, (Aug. 1980), pp. 249–254.
Sevier et al., Clin. Chem. vol. 27, No. 11, p. 1797–1806 (1981).
Maurer et al., "Proteins and Polypeptides as Antigens", in Methods in Enzymology, Helen Van Vunakis, Eds., Academic Press, New York, John J. Langone vol. 70, pp. 49–70, (1980).
Eager et al., "The Use of Conventional Antisera in the Production of Specific Monoclonal Antibodies," in Methods in Enzymology, Van Vunakis et al., eds, Academic Press, New York, vol. 121, pp. 59–69, (1986).
Towbin et al., J. Immunological Methods, vol. 72, pp. 313–340, (1984).
Tanaka, R.D. et al., "Molecular cloning of mevalonate kinase and regulation of its mRNA levels in rat liver", Proc. Natl. Acad. Sci. USA 87, 2872–2876 (1990).
Chiew, Y.E. et al., "Studies on pig liver mevalonate–5–diphosphate decarboxylase" Biochim. Biophys. Acta 916, 271–278 (1987).
Kohler and Milstein, Nature 256, 495–497 (1975) "Continuous cultures of fused cells secreting antibody of predefined specificity".

Lee, C. S. and O'Sullivan, W. J., Biochem. et Biophys. Act. 747, 215–224 (1983), "An improved purification procedure, an alternative assay and activation of mevalonate kinase by ATP".
Beytia, E. et al., J. Biol. Chem. 245, 5450–5458 (1970), "Purification and mechanism of action of hog liver mevalonic kinase".
Levy, H. R. and Popjak, J., Biochem. J. 75, 417–428 (1960), "Studies on the Biosynthesis of Cholesterol—Mevalonic Kinase and Phosphomevalonic Kinase from Liver".
Porter, J. W. Methods in Enzymol., vol. 110, p. 71 (1985), "Mevalonate Kinase" Dorsey, J. K. and Porter, J. W., J. Biol. Chem. 243, 4667–4670 (1968).
"The Inhibition of Mevalonic Kinase by Geranyl and Farnesyl Pyrophosphates", Flint, A. P. F., Biochem. J. 120, 145–150 (1970), "The Activity and Kinetic Properties of Mevalonate Kinase is Superovulated Rat Ovary".
Markley, K. and Smallman, E., Biochem. et Biophys. Acta 47, 327–335 (1961) "Mevalonic Kinase in Rabbit Liver".
Tanaka, R. D. et al., J. Biol. Chem. 265, 2391–2398 (1990), "Purification and Regulation of Mevalonate Kinase from Rat Liver".
Tanaka, R. D., talk given at the 1988 Aspen Hepatic Cholesterol and Lipoprotein Conference, Aug. 18–21, 1988 title only.
Popjak, G., Methods in Enzymology, vol. 15, 393–455 (1969), "Enzymes of Sterol Biosynthesis in Liver and Intermediates of Sterol Biosynthesis".
Tanaka, R. D. et al., Arteriosclerosis 9, 717a (1989), "The Regulation and Molecular Cloning of Mevalonate Kinase from Rat Liver".
Garcia–Martinez, J. et al., Revista Espanol de Fisiologica 38, 261–266 (1982), "Partial Purification and Properties and Properties of Mevalonate Kinase from Neonatal Chick Liver".

*Primary Examiner*—Frank C. Eisenschenk
*Attorney, Agent, or Firm*—Timothy J. Gaul; Audrey F. Sher

[57] ABSTRACT

Monoclonal antibodies which bind mevalonate kinase, hybrid cell lines which produce these monoclonal antibodies, and immunoassay methods for detecting mevalonate kinase using these monoclonal antibodies.

19 Claims, 1 Drawing Sheet

MONOCLONAL ANTIBODIES WHICH BIND MEVALONATE KINASE

BACKGROUND OF THE INVENTION

The fusion of mouse myeloma cells to spleen cells derived from immunized mice by Kohler and Milstein in 1975 [Nature 256, 495–497 (1975)] demonstrated, for the first time, that it was possible to obtain continuous cell lines making homogeneous (so-called "monoclonal") antibodies. Since this seminal work, much effort has been directed to the production of various hybrid cell lines (also called "hybridomas") and to the use of the antibodies made by these hybridomas for various scientific investigations. While the general technique for the preparation of hybridomas and monoclonal antibodies is well-known, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity.

Mevalonate kinase (EC 2·7·1·36; ATP: mevalonate-5-phosphotransferase) is a cytosolic enzyme in the cholesterol biosynthetic pathway which catalyzes the phosphorylation of mevalonate to form mevalonate-5-phosphate. Holloway, P. W. et al., Biochem J. 104, 57–70 (1967). Although mevalonate kinase has been described in animals and plants, very little is known about its regulation. However, there is some evidence to suggest that the regulation of mevalonate kinase may be involved in the regulation of cholesterol biosynthesis. The activity of mevalonate kinase is inhibited by geranyl pyrophosphate (GPP) and farnesyl pyrophosphate (FPP), which are intermediates in the cholesterol biosynthetic pathway after mevalonate kinase. GPP and FPP inhibit mevalonate kinase activity by binding competitively at the ATP-binding site on the enzyme, and it has been postulated that mevalonate kinase activity may be regulated by feedback inhibition from GPP and FPP. See, Dorsey, J. K. et al., J. Biol. Chem. 243, 4667–4670 (1968). However, further studies are needed to determine if mevalonate kinase plays a regulatory role in the cholesterol biosynthetic pathway.

Furthermore, mevalonic aciduria, a genetic disease involving the cholesterol biosynthetic pathway, has recently been discovered. There are six reported cases of mevalonic aciduria, and the genetic disease is transmitted as an autosomal recessive trait. Subjects with this disease have extremely high levels of mevalonate in their plasma and urine, and cells from these subjects have less than 10% of the normal levels of mevalonate kinase activity. Hoffman, G. et al., New Engl. J. Med. 314, 1610–1614, (1986); Brown, M. S. et al., J. Lipid Res. 21, 505–517 (1980).

Thus, it is readily apparent that the need exists in the art for materials and methods for the study of mevalonate kinase so that its role in the regulation of cholesterol biosynthesis may be ascertained. There is also a need for methods for the detection and study of the genetic disease mevalonic aciduria.

SUMMARY OF THE INVENTION

The present invention aids in solving these and other needs in the art.

The present invention concerns hybrid cell lines which produce monoclonal antibodies which bind mevalonate kinase.

The present invention further concerns monoclonal antibodies which bind mevalonate kinase.

The present invention additionally concerns immunoassay methods for detecting the presence of mevalonate kinase in a sample.

The present invention also concerns immunoassay methods for quantitatively determining the amount of mevalonate kinase in a sample.

DETAILED DESCRIPTION OF THE INVENTION

Figure 1:
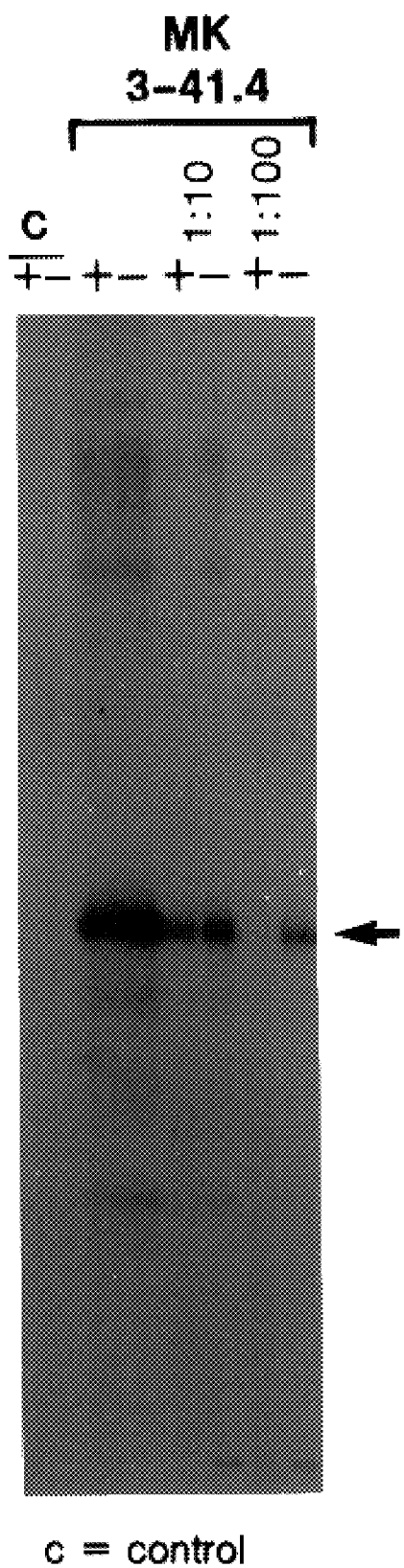
FIG. 1 shows the immunoprecipitation of mevalonate kinase when preincubated with monoclonal antibody MabMK3-41.

The present invention concerns hybrid cell lines, also called hybridomas, monoclonal antibodies and immunoassay methods utilizing these antibodies.

In particular, the present invention concerns hybrid cell lines which produce monoclonal antibodies which bind mevalonate kinase.

Particularly preferred is the hybrid cell line designated as MK3-41·4, which is a subclone of MK3-41, or hybrid cell lines which have the identifying characteristics of this hybrid cell line.

Hybrid cell line MK3-41·4 was deposited with the American Type Culture Collection, 12301 Parklawn Drive, Rockville, Md. 20852 on Jan. 16, 1990 under the Budapest Treaty and assigned ATCC accession no. HB 10323.

Also preferred are the hybrid cell lines designated as MK3-14, MK3-41, MK5-2, MK5-22, MK6-13, MK6-16, MK9-14, MK9-36 and MK9-55, or subclones derived therefrom, or hybrid cell lines which have the identifying characteristics of these hybrid cell lines.

The hybrid cell lines of the present invention may be produced by various methods generally known to those of ordinary skill in the art. In general, the method involves immunizing suitable mammals, for example mice, with the antigen of interest, in this case mevalonate kinase, fusing antibody producing cells isolated from the animal with myeloma cells, cloning the resulting hybrid cells and selecting those cells which produce the desired monoclonal antibody which binds the antigen of interest.

Immunizations are usually performed with purified antigens, in this case purified mevalonate kinase.

The usual mammals used for immunizations are mice, especially BALB/c mice, but other mammals and mouse strains may also be employed. The immunizations are performed in a manner known in the art, such as by administering parenterally, intraperitoneally, intravenously and/or subcutaneously, three to six injections each containing an appropriate amount of purified antigen (i.e, from about 1 $\mu$g to about 50 $\mu$g), at intervals of about one to six weeks, usually together with an adjuvant, for example, complete or incomplete Freund's adjuvant. While immunizations are generally performed in vivo, various in vitro procedures are also known and may be employed.

Antibody-producing cells of the immunized animals, usually spleen cells, are taken from the animals two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids. Myeloma cells that lack the enzyme hypoxanthine-guaninephosphoribosyl transferase (HGPRT) or the enzyme thymidine kinase (TK) and that, for that reason, do not survive in a selective culture medium containing hypoxanthine, aminopterin and thymidine (HAT medium), may be employed. Myeloma cells and cell lines prepared therefrom that do not survive in HAT medium and do not secrete any immunoglobulins or parts thereof, for example cell lines P3X63-Ag8.653 and Sp2/0-Ag14, may also be used. Various fusion-promoters, for example, Sendai virus or other paramyxoviruses, optionally in UV-inactivated form, calcium ion, surface-active lipids, such as isolecithin, or polyethylene glycol may also be employed. Myeloma cells are usually fused with a three- to twenty-fold excess of spleen cells from immunized animals in a solution containing from 30 to 50% polyethylene glycol (PEG) having a molecular weight of about 1000 to 4000. Exposure to PEG for about 2 to 3 minutes appears to be optimal to prevent toxicity to cells; temperatures of about 37° are recommended.

After fusion, the cells are partitioned out and cultured in selective HAT medium, with only hybrid cells surviving, since these combine, from the myeloma cells, the ability to grow in vitro and, from the antibody-producing cells of the immunized animals, the missing HGPRT or TK genes and, therewith, the ability to survive in HAT medium.

Suitable culture media for the growth of the hybridoma cells are the customary standard culture media, for example, Dulbecco's Modified Eagles Medium or Roswell Park Memorial Institute (RPMI) 1640 medium containing 10–15% fetal calf serum, supplemented with antibiotics. At the beginning of cell growth, so-called feeder cells, for example normal mouse peritoneal exudate cells, spleen cells, bone marrow macrophages or the like, may be added. At regular intervals, said culture media may be supplemented by selective HAT medium to prevent hybrid cells from being overgrown by ordinary myeloma cells still present after the initial HAT selection process.

The cell culture supernatants of the hybrid cells surviving HAT selection are examined for the presence of the desired monoclonal antibodies. Advantageously, the cell supernatants are tested in an immunoassay, for example, radioimmunoassay or enzyme immunoassay, that demonstrates the binding of monoclonal antibodies to the antigen of interest.

Those hybrid cells which produce antibodies having the desired specificity as well as other desirable characteristics can then be maintained as viable cultures and/or frozen for storage.

The present invention further concerns monoclonal antibodies which bind mevalonate kinase.

Preferred are the monoclonal antibodies designated as MabMK3-41, MabMK6-13, MabMK6-16, MabMK9-14, MabMK-9-55 and MabMK9-36, or monoclonal antibodies with the identifying characteristics of these monoclonal antibodies.

Particularly preferred is the monoclonal antibody designated as MabMK3-41.4, or monoclonal antibodies with the identifying characteristics of this monoclonal antibody.

Also preferred are substantially purified monoclonal antibodies which bind mevalonate kinase.

Additionally preferred are derivatives of monoclonal antibodies which bind mevalonate kinase.

The monoclonal antibodies of the present invention may be produced by various methods generally known to those of ordinary skill in the art. Hybrid cells producing such antibodies may be cultured in vitro and the monoclonal antibodies isolated from the culture supernatants, or may be multiplied in vivo in a suitable mammal, and the monoclonal antibodies isolated from the body fluids of that mammal. If desired, a monoclonal antibody resulting from either of these techniques may be converted into a derivative thereof.

Suitable culture media for in vitro culturing are the customary standard culture media, for example, Dulbecco's Modified Eagles Medium or RPMI 1640 medium containing 10 to 15% fetal calf serum and supplemented with antibiotics.

Large quantities of the desired monoclonal antibodies may also be obtained by multiplying the hybrid cells in vivo. For this purpose, antibody producing hybridomas are inoculated intraperitoneally into syngeneic mammals, and after 1 to 3 weeks, the antibodies are isolated from the ascites fluid of those mammals. For example, hybrid cells originating from BALB/c mice are injected intraperitoneally into BALB/c mice that have previously been pretreated intraperitoneally with a hydrocarbon such as 2,6, 10,14-tetramethylpentadecane (pristane) to irritate the peritoneal cavity, and, after 8 to 10 days, ascites fluid is withdrawn from these animals.

The monoclonal antibodies produced in vitro or in vivo may be purified using various methods, for example, gel filtration chromatography, ion-exchange chromatography, DEAE-cellulose chromatography or affinity chromatography. Optionally, selected proteins in the culture supernatants or ascites fluid, including the desired monoclonal antibodies, may be precipitated using specific concentrations of ammonium sulphate or the like before being subjected to chromatography.

If desired, derivatives of the monoclonal antibodies produced either in vitro or in vivo may be prepared.

Derivatives of monoclonal antibodies according to the invention include, for example, fragments, such as Fab, Fab' or F(ab')$_2$ fragments, that retain their specificity for the antigenic determinants of the antigen of interest, radioactively labelled monoclonal antibodies which are labelled, for example, with radioactive iodine ($^{125}$I, $^{131}$I), carbon ($^{14}$C), sulphur ($^{35}$S), tritium ($^3$H) or the like, and monoclonal antibodies conjugated with enzymes such as horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase. Additional derivatives include monoclonal antibodies labeled with fluorescent materials such as fluorescein or rhodamine, and monoclonal antibodies labelled with biotin.

Fragments of monoclonal antibodies according to the invention, for example, Fab, Fab' or F(ab')$_2$ fragments, that retain their specificity for the antigenic determinants of the antigen of interest, may be prepared according to generally known methods, for example, by fragmenting monoclonal antibodies by proteolytic digestion with enzymes such as pepsin or papain and/or by cleavage of disulphide bonds by chemical reduction.

Monoclonal antibodies radioactively labelled with iodine ($^{125}$I, $^{131}$I) may be obtained by iodination, for example, with radioactive sodium or potassium iodide after oxidization with a chemical oxidizing agent, such as sodium hypochlorite, chloramine T or the like, or an enzymatic oxidizing agent, such as lactoperoxidase and glucose oxidase. Radioactively labelled monoclonal antibodies according to the invention may also be prepared by adding, to the culture media for the in vitro culturing, in a known manner, radioactively labelled nutrients containing radioactive carbon ($^{14}$C), tritium ($^3$H), sulphur ($^{35}$S) or the like, for example, L-($^{14}$C)-leucine, L-($^{3}$H)-leucine or L-($^{35}$S )-methionine, and obtaining the monoclonal antibodies as described above.

Enzyme-conjugated monoclonal antibodies according to the invention may be obtained by various generally known methods, for example, by reacting monoclonal antibodies and the desired enzyme after modification with coupling reagents such as aldehydes, carbodiimides, maleimides, imidates, succinimides and pyridyl disulfides. Specific coupling agents include, for example, glutaraldehyde, periodate, N,N'-o-phenylenedimaleimide, N-(m-maleimidobenzoyloxy)-succinimide, N-(3-(2'-pyridyldithio)-propionoxy)-succinimide or the like.

Various enzyme substrates, for example 5-aminosalicyclic acid, O-phenylenediamine, 3,3'-dimethoxybenzidine, and 2,2'-azino-bis-(3)-ethylbenzothiazolin-6-sulphonic acid for horseradish peroxidase and p-nitrophenyl phosphate for alkaline phosphatase, may be used in conjunction with the enzyme-conjugated antibodies.

It is contemplated that the present invention encompasses all monoclonal antibodies exhibiting the characteristics of the monoclonal antibodies described herein. The monoclonal antibodies described herein belong to the class IgM, and the subclasses $IgG_1$, $IgG_{2a}$ and $IgG_{2b}$. It is contemplated that antibodies having the patterns of reactivity illustrated herein are included within the scope of the present invention regardless of the immune globulin class or subclass to which they belong. For example, a monoclonal antibody exhibiting the characteristics described herein may be of the subclass $IgG_1$, $IgG_2$a, $IgG_2$b, or $IgG_3$, or of classes IgM, IgA, or of other known Ig classes.

Furthermore, since the hybrid cell line produced from a known mouse myeloma cell line and spleen cells from a known species of immunized mouse cannot be further identified except by reference to the antibody produced by the hybrid cell line, it is contemplated that all hybrid cell lines producing antibodies having the reactivity characteristics described above are included within the scope of the present invention.

The present invention further concerns immunoassay methods utilizing monoclonal antibodies and derivatives thereof which bind mevalonate kinase for the qualitative and quantitative determination of mevalonate kinase, especially in a biological sample.

Particularly preferred is a qualitative immunoassay method for detecting the presence of mevalonate kinase in a sample comprising:

(a) incubating the sample with a monoclonal antibody which binds to the mevalonate kinase; and (b) detecting the presence of immune complexes formed by the mevalonate kinase and the monoclonal antibody.

Additionally preferred is an immunoassay method for quantitatively determining the amount of mevalonate kinase in a sample comprising:

(a) incubating the sample with a monoclonal antibody which binds to the mevalonate kinase;

(b) determining the amount of immune complexes formed by the mevalonate kinase and the monoclonal antibody; and (c) correlating the amount of immune complexes formed with the amount of mevalonate kinase present in the sample.

The immunoassay method of the present invention may be a radioimmunoassay (RIA) which utilizes, depending on the particular protocol employed, unlabeled or radioactively labeled derivatives of monoclonal antibodies which bind either alone or in combination. In the case where the monoclonal antibody which binds mevalonate kinase is unlabeled, a different detectable marker, for example, a radiolabeled antibody which is capable of binding the monoclonal antibody which binds mevalonate kinase, may be employed. Any of the known modifications of RIA, for example, homogeneous RIA, heterogeneous RIA, competitive RIA, and sandwich RIA, may be employed. Also contemplated are immunoblotting immunoassay techniques such as western blotting employing a radioactive detection system.

The immunoassay method of the present invention may also be an enzyme immunoassay (EIA) which utilizes, depending on the particular protocol employed, unlabeled or enzyme-labeled derivatives of monoclonal antibodies which bind mevalonate kinase, either alone or in combination. In the case where the monoclonal antibody which binds mevalonate kinase is not enzyme labelled, a different detectable marker, for example, an enzyme-labeled antibody capable of binding to the monoclonal antibody which binds mevalonate kinase, may be employed. Any of the known modifications of EIA, for example, enzyme-linked immunoabsorbent assay (ELISA), may be employed. Also contemplated by the present invention are immunoblotting immunoassay techniques such as western blotting employing an enzymatic detection system.

The immunoassay method of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection system.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. The amount of antibody which binds mevalonate kinase is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The monoclonal antibodies of the present invention may also be used to purify mevalonate kinase. Briefly, monoclonal antibodies which bind mevalonate kinase may be bound to a substrate (e.g., a solid support such as Protein-A Sepharose), and contacted with a material (e.g., a solution) containing mevalonate kinase under conditions permitting the monoclonal antibodies to bind the mevalonate kinase. Any unbound material is separated from the immobilized monoclonal antibodies, and the bound mevalonate kinase eluted from the monoclonal antibodies with a suitable eluant to yield purified mevalonate kinase.

The purified mevalonate kinase may then be used to screen for mevalonate kinase inhibitors. The mevalonate kinase binding monoclonal antibodies may also be used to assay for the degree of inhibition of mevalonate kinase produced by inhibitors of mevalonate kinase or inhibitors of the enzymes in the cholesterol biosynthetic pathway. Other uses of the mevalonate kinase binding monoclonal antibodies include detecting genetic abnormalities of mevalonate kinase resulting in either alteration of protein structure or activity, monitoring the level of mevalonate kinase in crude extracts, and utilizing the monoclonal antibodies in immunoblotting procedures.

The following examples are further illustrative of the present invention. These examples are not intended to limit the scope of the present invention and provide further understanding of the invention.

EXAMPLE I
Cell Culture

The mouse myeloma (plasmacytoma) cell line, Sp2/0-Ag14, deficient in hypoxanthine guanine phosphoribosyl transferase (HGPRT) was employed. This cell line is available from the American Type Culture Collection (Rockville, Md.) and the National Institute of General Medical Sciences Human Genetic Mutant Cell Repository (Camden, N.J.). Sp2/0 cells and selected hybridomas were cultured at 37° C. in a humidified 8% $CO_2$ atmosphere in Dulbecco's Modified Eagles Medium (DMEM) with high glucose (4.5 g/liter) supplemented with 10% fetal calf serum and L-glutamine (0.3 mg/ml). DMEM and L-glutamine were obtained from Gibco Laboratories (Life Technologies Inc., Grand Island N.Y.) and fetal calf serum was obtained from Hyclone Laboratories Inc., Logan, Utah. All other medium constituents were obtained from Sigma Chemical Company, St. Louis, Mo., unless otherwise indicated. After the fusion, cells were grown in HY medium (HY medium: DMEM supplemented with 10% NCTC 109 (Gibco), 15% fetal calf serum, 0.2 units bovine insulin/ml, 0.45 mM pyruvate, 1 mM oxaloacetate and 0.1% glutamine) containing hypoxanthine (0.1 mM), aminopterin (0.1 $\mu$m) and thymidine (0.16 mM).

EXAMPLE 2
Production of Monoclonal Antibodies

Immunizations were with purified rat mevalonate kinase (immunogen) isolated from the livers of rats that had been fed a diet supplement with 1.0% pravastatin. During the mevalonate kinase purification procedure, mevalonate kinase activity was measured using a spectrophotometric assay as described by Popjak, G., Methods Enzymol. 15, 393–453 (1969). The reaction mixture for the assay contained 100 mM potassium phosphate buffer (pH 7.0), 10 mM KF, 10 mM $MgCl_2$, 10 mM dithiothreitol (DTT), 0.5 mM NADH, 1 mM phosphoenolypyruvate (Boehringer Mannheim Biochemicals, Indianapolis, Ind.), 2 mM ATP, 20 units of pyruvate kinase (Boehringer Mannheim), 27 units of lactate dehydrogenase (Boehringer Mannheim) and 3 mM RS-mevalonate (Sigma), a mevalonate kinase substrate. Final volume of the reaction mixture was 1 ml. Enzyme assays were conducted at 25° C. on a Perkin Elmer Lambda 3B dual-beam spectrophotometer. The background rate of NADH oxidation was measured for 60 seconds, then mevalonate was added and the reaction rate was measured for an additional 60 seconds. One unit of enzyme activity was defined as the amount of activity required to produce 1 $\mu$mol of mevalonate-5-phosphate per minute. Enzyme activity measured in the spectrophotometric assay was proportional to the amount of protein in the assay up to a final concentration of approximately 200 $\mu$g/ml. Protein concentration was determined by the method of Bradford, M., Anal. Biochem. 72, 248–254 (1976). Immunogen was prepared in the following manner.

Female Sprague-Dawley rats (80 g body weight, CAMM Laboratories, Wayne, N.J.) were acclimated to a 12 hour light/12 hour dark cycle for 14 days. After acclimation, the rats (n=7) were treated for 15 days with a diet containing 5% cholestyramine (Bristol Laboratories, Wallingford, Conn.) and 1% pravastatin (E.R. Squibb and Sons, Inc.), and then they were sacrificed at the last hour of the dark cycle. The livers were quickly excised and homogenized in 1.5 volumes of ice-cold buffer A (0.1M sucrose, 50 mM KCl, 30 mM dipotassium EDTA, 10 mM DTT, 0.1 mM leupeptin (Sigma) and 40 mM potassium phosphate buffer, pH 7.2) using a glass, Potter-Elvejhem homogenizer with a motor driven teflon pestle. Liver homogenates were centrifuged at 10,000×g for 10 minutes at 50° C., and the supernates were collected and recentrifuged under identical conditions. The supernates were then centrifuged at 100,000×g for 45 minutes at 5° C. The 100,000×g supernates were collected and kept at 0° C., saturated ammonium sulfate (pH 7.4) was slowly added to a final concentration of 45%, and the precipitate was collected by centrifugation at 17,500×g for 15 minutes at 5° C. After decanting the supernate, the pellet was dissolved in buffer B (10 mM DTT and 20 mM Tris, pH 7.5) and then centrifuged at 19,000×g for 60 minutes at 5° C. The supernate was collected and loaded onto a Blue Sepharose column (2.5×10 cm) (Pharmacia LKB Biotechnology, Inc., Piscataway, N.J.) which was equilibrated with buffer B at room temperature. Unbound material was removed by washing with 60 ml of buffer B and then approximately 500 ml of buffer B containing 0.1M KCl. Mevalonate kinase activity was eluted from the column using a linear salt gradient of 0.1M to 1M KCl in buffer B. Fractions which contained enzyme activity were pooled and the enzyme was precipitated with 60% ammonium sulfate (pH 7.4). The precipitate was collected by centrifugation at 17,500×g for 15 minutes at 5° C., the pellet was dissolved in buffer C (10 mM DTT and 20 mM N-[2-acetamido]-2-iminodiacetic acid (ADA), pH 7.0) and centrifuged at 19,500×g for 45 minutes at 5° C. The supernate was collected and loaded onto a Sephadex G-150 column (2.5×44.5 cm) (Pharmacia) which was equilibrated and washed in buffer C at room temperature. Fractions containing mevalonate kinase activity were pooled and loaded directly onto an ATP-agarose column (1.5×4.5 cm) (Sigma) which was equilibrated with 10 mM DTT (pH 7.0) at room temperature. The column was washed with 10 mM DTT, and then the enzyme was eluted with 10 mM DTT containing 15 $\mu$M FPP [farnesyl pyrophosphate; prepared as described in Davisson et al., Methods Enzymol. 110, 130–144 (1985)]. Potassium phosphate (pH 7.0) was added to each column fraction to yield a final concentration of 0.1M. The fractions containing mevalonate kinase activity were collected and stored at 5° C.

The rat mevalonate kinase so purified appeared homogeneous, since only one protein-staining band (silver staining) was observed after the enzyme was electrophoresed on SDS-poly-acrylamide gels, and only one protein-staining band (silver staining) was observed after isoelectric focusing.

After purification, the enzyme was stable for several months when stored at 5° C. in buffer containing 10 mM DTT. The mevalonate kinase irreversibly lost all enzyme activity after freezing. The activity of rat mevalonate kinase was also sensitive to pH, and nearly all enzyme activity was lost when the pH was lower than 6.

BALB/c mice were hyperimmunized with doses of 15–25 ug of immunogen at 3–4 week intervals. The immunogen was emulsified in complete Freund's adjuvant for the first immunization and emulsified in incomplete Freund's adjuvant for the second immunization. The route of immunization for these doses was subcutaneous and intraperitoneal. All subsequent immunizations were completed in saline (150 mM NaCl) and injected intraperitoneally. Mice were immunized at 3–4 week intervals, bled and the resultant sera analyzed for the presence of antibodies recognizing the immunogen by ELISA (enzyme-linked immunosorbent assay) and by Western blotting methods. Mice having the highest serum titers were selected for fusions. Mice selected for fusion were rested for a period of six months and then immunized with the purified immunogen in saline for the three days prior to performing the fusion.

Fusions were performed according to a modification of the method of Kohler and Milstein Nature, 256, 495–497 (1975), using Koch-light polyethylene glycol 4000. Spleen cells from the selected animals were collected by perfusion with medium introduced by a syringe and erythrocytes lysed in cold 0.17M $NH_4Cl$. The collected cells were counted, mixed at a ratio of $10^8$ spleen cells to $2 \times 10^7$ myeloma cells in a round-bottom tube. The cell mixture was washed in medium free of serum by centrifugation. All supernatant liquid was removed by suction and the pellet loosened. 0.5 ml of PEG solution (30% polyethylene glycol, 5% dimethylsulfoxide in medium without serum) was slowly added to the pellet. The cells were maintained in the PEG solution for 8 minutes during which time they were pelleted at 1000 rpm for 5–6 minutes. Medium without serum (5 mls) was slowly added to disperse the pellet followed by the addition of 5 mls of HY medium containing 15% fetal calf serum. The cells were pelleted and evenly resuspended in HY medium supplemented with hypoxanthine, aminopterin and thymidine resulting in a cell suspension of $1.5 \times 10^6$ cells per ml. Cells were then plated out in 96-well microtiter plates (100 µl/well) and placed in a humidified $CO_2$ incubator at 37° C. The wells were refed 6–7 days later. Clones growing in selection medium in microtiter plate wells were identified by examining the plate macroscopically using an inverted mirror stand. Medium from wells containing these clones was tested for the presence of specific antibody by ELISA (See Example 4).

EXAMPLE 3
Expansion of Antibody Producing Hybridomas

Hybridomas producing specific antibody as demonstrated by ELISA were expanded by standard cell culture techniques and grown for several passages in HY media supplemented with hypoxanthine and thymidine. Cells were adapted to Dulbecco's Modified Eagle's medium supplemented with 10% calf serum and glutamine (0.1%). Hybridomas of interest were subcloned by limiting dilution in freshly prepared HY media; clones were screened by ELISA (See Example 4). Subcloned hybridomas and the original lines were cryopreserved by standard techniques using a freezing mixture of 95% calf serum with 5% dimethylsulfoxide.

Antibody was collected in cell culture supernatant by accumulating antibody from densely growing cultures. In addition to cell culture methods, hybridomas were also grown in the peritoneal cavity of syngeneic BALB/c mice. Mice were injected intraperitoneally with 0.5 ml of pristane (2, 6, 10, 14-tetramethyldecanoic acid, Aldrich Chemical Company, Inc., Milwaukee, Wisc.) at least 10 days prior to injection with the hybridoma line of interest. Hybridomas (approx. $4 \times 10^6$ cells) shown to have activity in an ELISA prior to injection were inoculated intraperitoneally into the pristane treated BALB/c mice to produce ascites fluid. Ascites fluid was removed from the mice after 7–10 days and clarified by centrifugation at 35000 rpm in a Beckman 50Ti rotor at 6° C. Clarified ascites was stored at 4° C. with 0.02% sodium azide or frozen in aliquots at −70° C.

EXAMPLE 4
Enzyme Linked Immunosorbent Assay (ELISA)

Sera from immunized mice and media collected from wells containing HAT selected hybridomas were tested for the presence of antibodies recognizing rat mevalonate kinase. Partially purified mevalonate kinase was diluted in 0.05M sodium carbonate buffer (pH 9.76) to 8 µg/ml. 50 µl of this solution was added per well of a distilled water-rinsed Nunc Immuno Plate IF 96-well plate (A/S Nunc, Kamstrup, Denmark) and sealed. After incubation overnight at 4° C., the plates were rinsed six times with PBS-Tw20 (phosphate buffered saline with 0.05% Tween 20). Undiluted media (50 µl) or diluted mouse sera (50 µl) were incubated for two hours at room temperature. Unbound mouse antibodies were removed by washing the plates six times with the PBS-Tw20 wash. After washing, 100 µl of diluted horseradish peroxidase conjugated-goat anti-mouse immunoglobulin IgG (heavy and light chain) (organon Teknika-Cappel, Malvern, Pa.) was added per well for a period of two hours at room temperature. Antisera was diluted to 1:8000 in ELISA buffer consisting of PBS-Tw20 supplemented with 20.4 g sodium chloride per liter, 0.29 g EDTA per liter and 0.2% peroxidase-free bovine serum albumin. Removal of unbound conjugate was accomplished by extensive washings with PBS-Tw20. Bound conjugate was detected by visualization using a TMB (3, 3', 5, 5' tetramethylbenzidine) substrate kit (TMB Microwell Peroxidase Substrate System, Kirkegaard and Perry, Gaithersburg, Md.). Equal volumes of the TMB Peroxidase Substrate Solution and Peroxidase Substrate Solution B with hydrogen peroxide were mixed immediately prior to addition to the wells of the 96-well plate. 100 µl of the substrate was added per well and the reaction allowed to proceed for 15 minutes. The reaction products measured by optical densities were recorded on a Titertek Multiskan PLUS microtiter plate reader (Flow Laboratories, Inc., McLean, Va.) at 650 rm. The reactions were stopped by the addition of 50 µl of 1M HCl and the reactions read at 450 nm.

EXAMPLE 5
Determination of Immunoglobulin Class/Subclass

To determine the immunoglobulin class/subclass of the hybridomas, cell culture supernatant containing antibody was assayed in an ELISA format. Affinity purified goat anti-mouse immunoglobulin (heavy and light chain) (Organon Teknika-Cappel) was diluted 1:800 in 0.05M sodium carbonate buffer, pH 9.76. 50 µl of this solution was added per well of a distilled water-rinsed Nunc Immuno Plate 1F and incubated 2 hours at room temperature or overnight at 4° C. Unabsorbed antibody was removed by washing with PBS-Tw20. Fifty microliters of antibody-containing supernatant or diluted myeloma ascites controls were added and incubated for a period of two hours at room temperature. Unbound antibody was removed by extensive washings. Alkaline phosphatase conjugated goat anti-mouse immunoglobulin class and subclass specific reagents (FisherBiotech, Orangeburg, N.Y.) were diluted 1:500 in PBS-Tw20 buffer with 0.2% bovine serum albumin. One hundred microliters of each conjugate was added to a well previously incubated with the anti-mouse Ig and the mouse antibody of interest. The alkaline phosphatase conjugate was incubated for two hours at room temperature and the plates washed four times with PBS-Tw20 followed by four washes of Tris buffered saline (0.05M Tris HCl, 0.15M NaCl pH 7.5). Alkaline phosphatase activity was visualized using p-nitrophenyl phosphate (1 mg/ml) diluted in alkaline phosphatase buffer (10 mM diethanolamine containing 0.5 mM MgCl). The product of the reaction was scored by eye or quantitated at 405 nm with a Titertek Multiskan PLUS microtiter plate reader.

EXAMPLE 6
Monoclonal Antibody Purification

About 2 to 4 mls of ascites fluid produced from the appropriate hybridoma was diluted 1:1 with Binding Buffer supplied by Bio Rad in their Bio-Rad Affi-Gel Protein A MAPS II Kit (Bio-Rad Laboratories, Richmond, Calif.) and applied to a 1 cm×5 cm Affi-Gel Protein A column pre-equilibrated with Binding Buffer. Diluted ascites was applied at a rate of 0.2–0.3 ml/minute. Effluent was collected and reapplied to the column prior to washing. The elution of bound antibody was carried out using the Bio-Rad Elution Buffer at a rate of 0.5 ml/minute. Fractions were neutralized immediately by the addition of 1M Tris HCl, pH 9.0. Elution of immunoglobulin was monitored by determining the absorbance of each sample at 280 nm. Samples showing significant protein levels were pooled and dialyzed against PBS at 4° C. The protein concentration was calculated using an extinction coefficient for immunoglobulin of $E=1.4$ cm$^2$/mg. Antibody activity was determined using the ELISA described above. Purity of the immunoglobulin was determined by agarose gel electrophoresis by the Paragon system (Beckman Instruments, Fullerton, Calif.) and standard sodium dodecyl sulfate-polyacrylamide gel electrophoresis.

EXAMPLE 7
Analytical Methods

Sodium dodecyl sulfate-polyacrylamide gel electrophoresis (SDS-PAGE) was performed using gels and buffers described by Laemmli, U.K., "Cleavage of Structural Proteins During Assembly of the Head of Bacteriophage $T_4$", Nature, 227:680–685 (1970). Samples were prepared in a buffer containing β-mercaptoethanol and SDS, heated and subjected to electrophoresis.

Immunoblotting was performed on crude extracts and purified rat mevalonate kinase electrophoresed by SDS-PAGE and electrophoretically transferred to nitrocellulose sheets according to the method of Towbin, H. T., Staehelin, T. and Gordon, J., "Electrophoretic transfer of protein from polyacrylamide gels to nitrocellulose sheets: Procedure and some applications", Proc. Natl. Acad. Sci. (USA), 76:4350–4354 (1979). The nitrocellulose membrane was blocked with either 5% BSA (fraction V) or 0.2% dry milk prepared in Tris-buffered saline (0.02M Tris HCl, 0.5M NaCl, pH 7.5) for 30–60 minutes at room temperature with agitation. The blocked nitrocellulose membrane was then either cut into strips for incubation with antibody containing supernatant or diluted antiserum or placed into a Miniblotter manifold (Immunetics, Cambridge, Mass.) and appropriate antibodies added to the channels. Incubation with the first antibody was carried out at room temperature with agitation for 1–2 hours. Several washes with TBS were done to remove unbound antibody. An alkaline phosphatase conjugated affinity purified goat anti-mouse IgG (heavy and light chains) reagent (Jackson ImmunoResearch Laboratories, Inc., West Grove, Pa.) was diluted 1:3000 in TBS containing 0.05% Tween 20 and 1% gelatin and added to the blot and incubated 1–2 hours at room temperature with agitation. Again the blot was extensively washed with TBS before addition of substrate. The sites of enzyme binding was detected by the use of BCIP/NBT (5-bromo-4-chloro-3-indolyl phosphate/nitroblue tetrazolium) substrate supplied in kit form from Kirkegaard and Perry (Gaithersburg, Md.).

EXAMPLE 8
Identification and Characterization of Monoclonal Antibodies

Mice immunized with a preparation of mevalonate kinase had developed significant levels of antibody following several immunizations. Sera from the mice were tested for the presence of antibodies recognizing mevalonate kinase by ELISA as well as by immunoblotting. The spleen of a responding animal was removed and fused with the myeloma line as described above. Over 59% of the wells plated produced HAT resistant clones distinguishable by light microscopy; antibody producing hybridomas (prefixed MK; subclones denoted by .1-.n, for example, MK-3-41 with subclones MK3-41.4 and MK3-41.1) were identified by ELISA. Thirty-one clones were initially identified; twelve clones continued to produce antibodies following expansion and subcloning. The antibodies (prefixed MabMK; antibodies produced by subclones denoted by .1-.n, as above) were characterized by determination of specificity with various available proteins. The antibodies were tested for antibody reactivity to β-galactosidase, bovine serum albumin, atrial natriuretic factor, bovine thyroglobulin and untreated polystyrene following the same format used for the mevalonate kinase ELISA described above. Several of the monoclonal antibodies bound to the unrelated proteins and were discarded. The specificity of the MK antibodies to mevalonate kinase vs. the other unrelated proteins measured in terms of binding in an ELISA ranged from approximately 4 fold to 20 fold (Table 1). The heavy chain isotype and light chain class were determined by ELISA as described above. This data is listed in Table 1. All of the antibodies presumed to be specific to rat mevalonate kinase based upon the ELISA specificity data were analyzed for reactivity in immunoblotting analysis and results given in Table 1. A single polypeptide of $M_r$ 43 Kd was visualized with the monoclonal antibodies. The molecular weight of this protein is in agreement with the expected molecular weight of mevalonate kinase. Antisera prepared to this protein detected a polypeptide of the same molecular weight. Since this technique involves denaturation of the antigen, recognition by the monoclonal antibodies suggests that the epitopes recognized are either denatured epitopes or denaturation-resistant epitopes. Experiments described later indicate that these antibodies recognize denaturation-resistant epitopes.

In order to determine the nature of the epitope recognized by the individual mevalonate kinase monoclonal antibodies, an additive binding assay was performed that would identify those monoclonal antibodies binding to the same or spatially close determinants. Based upon these results, it is suggested that all of the antibodies bind to determinants that are very close. Antibodies MabMK5-2 and MabMK5-22 may have overlapping epitopes, antibodies MabMK9-55 and MabMK9-14 may overlap in a different region. The results suggest that antibodies MabMK6-13 and MabMK9-36 share a determinant also identified by antibody MabMK3-14 although a portion of the antibody combining site has an overlapping epitope with MabMK5-2 (and Mab MK5-22). Antibodies MabMK9-55 (MabMK9-14) appear to be in close proximity to the binding site of MabMK3-41 which is in close proximity to MabMK5-2.

Confirmation of the monoclonal antibody specificity to mevalonate kinase was performed by immunoprecipitation followed by immunoblotting analysis. Antibody-containing supernatant from MK3-41.4 and SP2 (C) were pre-incubated for 18 hours at 4° C. with (+) and without (−) 1.5 micrograms of purified mevalonate kinase. Supernatants were microfuged to remove particulate matter. A Western blot containing mevalonate kinase transferred to nitrocellulose was used to detect remaining anti-MK activity in the pre-incubated supernatant. Mouse immunoglobulins were detected with an alkaline phosphatase conjugated reagent and detected with the chromogenic substrate BCIP/NBT. The absorbed antibody successfully immunoprecipitated mevalonate kinase as a function of the concentration of the antibody added (FIG. 1). Note the absorption of anti-mevalonate kinase activity with decreasing amounts of immunoglobulin.

mevalonate kinase or, as a control, a monoclonal antibody against the EGF-receptor (Sigma Chemical Co.) were bound to Protein-A Sepharose beads (Pharmacia) (200 µl) by incubation for 4 hours at 37° C. Pure mevalonate kinase (5 µg) was then added to each preparation of antibody coupled to Protein-A Sepharose beads, and as a second control, 5 µg of enzyme was also added to a sample of Protein-A Sepharose beads alone. All samples were incubated at 37° C. for 30 minutes, the reaction mixtures were centrifuged at 13,700×g for 5 minutes, and the supernatant fractions were assayed for mevalonate kinase activity as described above. Mevalonate kinase enzymatic activity was shown to be removed by MabMK6-16.

TABLE 1

Mevalonate kinase Monoclonal Antibodies:
Specificity and Immunoglobuling Class Analysis

| Monoclonal Antibody | Isotype | ELISA[a] | | | | | | Immuno-blotting |
| | | MK[b] | Bgal[c] | BSA | BTG[d] | ANF[e] | plastic | |
|---|---|---|---|---|---|---|---|---|
| MabMK3-14 | IgM,k | +++ | + | − | − | − | − | − |
| MabMK3-41 | IgG1,k | ++++ | − | − | − | − | − | + |
| MabMK5-2 | IgG2b,k | +++ | − | + | − | − | − | − |
| MabMK5-22 | IgM,k | +++ | − | − | − | − | − | − |
| MabMK6-13 | IgM,k | ++++ | − | − | + | − | − | + |
| MabMK6-16 | IgG2a,k | ++++ | − | − | + | − | − | + |
| MabMK9-14 | IgM,k | ++++ | − | − | − | − | − | + |
| MabMK9-36 | IgM,k | ++++ | − | − | − | − | − | − |
| MabMK9-55 | IgG1,k | ++++ | − | − | − | − | − | + |

[a]ELISA $A_{650}$ nm data: <0.2 = −; 0.21–0.4 = +; 0.41–0.8 = ++; 0.81–1.2 = +++; 1.21–2.0 = ++++.
[b]MK = rat mevalonate kinase
[c]Bgal = β-galactosidase
[d]BTG = bovine thyroglobulin
[e]ANF = atrial natriuretic factor Further characterization has shown that the antibodies active in immunoblotting do not show any cross-reactivity to yeast mevalonate kinase.

EXAMPLE 9
Immunoblotting Using Anti-Mevalonate Kinase Antibodies

The mevalonate kinase monoclonal antibodies reactive in immunoblotting such as MabMK9-55 were used in the identification and quantitation of rat mevalonate kinase in crude liver extracts prepared from rats fed pravastatin using the procedure described in Example 7. This antibody was able to detect mevalonate kinase in the crude extract in the range of 24–50 nanograms, approximately 1–2% of the protein in the crude extract. This level of sensitivity was achieved using as a second antibody an alkaline phosphatase conjugated anti-mouse immunoglobulin. In addition, all of the immunoblot-reactive monoclonal antibodies were able to selectively identify rat mevalonate kinase from yeast mevalonate kinase in crude extracts from a yeast expression system. Due to the close homology of rat and human mevalonate kinase, these antibodies should prove useful in the identification of human mevalonate kinase.

EXAMPLE 10
Purification of Mevalonate Kinase

The monoclonal antibodies to rat mevalonate kinase have proven useful in the purification of the rat enzyme. Monoclonal antibody MabMK6-16 (30 µg) directed against rat

What is claimed is:

1. A hybrid cell line that produces a monoclonal antibody which is capable of binding rat mevalonate kinase.

2. The hybrid cell line according to claim 1 designated MK3-41, or subdones derived therefrom.

3. The hybrid cell line with all of the identifying characteristics of the hybrid cell line according to claim 2.

4. The monoclonal antibody secreted by the hybrid cell line according to claims 2 or 3.

5. The monoclonal antibody secreted by the hybrid cell line according to claim 1.

6. The monoclonal antibody according to claim 5 selected from the group consisting of IgG or IgM.

7. The monoclonal antibody according to claim 5 which is a murine monoclonal antibody.

8. The monoclonal antibody according to claim 5 designated MabMK3-41.

9. The monoclonal antibody with all of the identifying characteristics of the monoclonal antibody according to claim 8.

10. The monoclonal antibody according to claims 5 or 8 which has been derivatized by labeling with a detectable marker.

11. The monoclonal antibody according to claim 10 has been labeled with wherein the detectable marker is a radioisotope.

12. The monoclonal antibody according to claim 10 wherein the detectable marker is an enzyme.

13. The monoclonal antibody according to claims 5 or 8 which has been purified.

14. An immunoassay method for detecting the presence of mevalonate kinase in a sample comprising:

(a) incubating the sample with a monoclonal antibody which is capable of binding to rat mevalonate kinase; and (b) detecting the presence of immune complexes formed by the mevalonate kinase and the monoclonal antibody.

15. An immunoassay method for quantitatively determining the amount of mevalonate kinase in a sample comprising:

(a) incubating the sample with a monoclonal antibody which is capable of binding to rat mevalonate kinase;

(b) determining the amount of immune complexes formed by the mevalonate kinase and the monoclonal antibody; and (c) correlating the amount of immune complexes formed with the amount of mevalonate kinase present in the sample.

16. The immunoassay method according to claims 14 or 15 which is a radioimmunoassay.

17. The immunoassay method according to claims 14 or 15 which is an enzyme immunoassay.

18. The immunoassay method according to claims 14 or 15 which is an immunoblotting assay.

19. An antigen binding fragment of the monoclonal antibody according to claims 5 or 8.

* * * * *